(12) United States Patent
Ahn et al.

(10) Patent No.: US 6,980,284 B2
(45) Date of Patent: Dec. 27, 2005

(54) CONDENSATION PARTICLE COUNTER

(75) Inventors: Kang-Ho Ahn, Seoul (KR); Sang-Soo Kim, Seoul (KR); Hae-Young Jeong, Taejon (KR)

(73) Assignee: Hyundai Calibration & Certification Technologies Co., Ltd., Kyunggi-Do (KR)

( * ) Notice: Subject to any disclaimer, the term of this patent is extended or adjusted under 35 U.S.C. 154(b) by 29 days.

(21) Appl. No.: 10/381,251

(22) PCT Filed: Sep. 20, 2001

(86) PCT No.: PCT/KR01/01578

§ 371 (c)(1),
(2), (4) Date: Mar. 24, 2003

(87) PCT Pub. No.: WO02/29382

PCT Pub. Date: Apr. 11, 2002

(65) Prior Publication Data

US 2004/0012772 A1    Jan. 22, 2004

(30) Foreign Application Priority Data

Sep. 25, 2000 (KR) ............................... 2000/56163

(51) Int. Cl.[7] ............................................. G01N 1/00
(52) U.S. Cl. ..................... 356/37; 356/335; 356/336
(58) Field of Search .................... 356/38, 336–343, 356/37

(56) References Cited

U.S. PATENT DOCUMENTS

| | | | | |
|---|---|---|---|---|
| 4,293,217 A | * | 10/1981 | Bird et al. | 356/37 |
| 5,118,959 A | * | 6/1992 | Caldow et al. | 250/573 |
| 5,239,356 A | | 8/1993 | Hollander et al. | |
| 5,537,879 A | * | 7/1996 | Malczewski et al. | 73/863.61 |
| 5,872,622 A | * | 2/1999 | Schildmeyer et al. | 356/37 |
| 5,922,976 A | | 7/1999 | Russell et al. | |
| 6,263,744 B1 | | 7/2001 | Russell et al. | |
| 6,469,780 B1 | * | 10/2002 | McDermott et al. | 356/37 |
| 6,567,157 B1 | * | 5/2003 | Flagan et al. | 356/37 |

FOREIGN PATENT DOCUMENTS

JP          03-99248        4/1991

* cited by examiner

*Primary Examiner*—Michael P. Stafira
(74) *Attorney, Agent, or Firm*—Lowe Hauptman & Berner, LLP

(57) ABSTRACT

A condensation particle counter measures the number of ultra-fine particles by growing the ultra-fine particles through a condensing process. The counter includes a capillary in which vapor of operating liquid is condensed and the ultra-fine particles grow. An insulating material surrounds the capillary to shut out heat flow between the capillary and the environment. The condensation particle counter can use various operating liquids including alcohol and water, and can be also applied to semiconductor clean rooms.

18 Claims, 2 Drawing Sheets

CONDENSATION PARTICLE COUNTER

TECHNICAL FIELD

The present invention relates to a particle counter, and more particularly, to a condensation particle counter which measures the number of ultra-fine particles by growing the ultra-fine particles having their sizes of 0.1 µm or less which are used as condensation nuclei.

BACKGROUND ART

Measurement of the number of ultra-fine particles is prerequisite to fundamental study of the particles for air pollution measurement, and has also been applied to investigation of the cause why the ultra-fine particles have been generated in semiconductor clean rooms and the like so that the clean rooms can be kept at a clean state by removing the ultra-fine particles from the clean rooms. As well known in the art, an optical instrument such as a laser is utilized to measure the number of the ultra-fine particles. In general, a particle measurement limit of the optical instrument corresponds to about 0.1 µm in particle size. Thus, a condensation particle counter has been utilized for measuring the ultra-fine particles having their sizes of 0.1 µm or less beyond such a measurement limit. The principle of the condensation particle counter is that a liquid is condensed around the ultra-fine particles by utilizing the ultra-fine particles as condensation nuclei, and then, the ultra-fine particles are caused to grow to such a degree that they can be measured through the optical instrument.

In order to cause the liquid to be condensed around the ultra-fine particles, the following three types of technologies are currently utilized. The first one is an oldest technology. According to this technology, particles to be measured are injected into a container with water contained therein, the container is hermetically closed, and then, inside pressure of the container is rapidly reduced. Thus, inner temperature of the container is rapidly decreased, and temperature of water vapor within the container is consequently lowered. As a result, the vapor becomes supersaturated. The vapor starts to be condensed under such a supersaturated state, and is then condensed around the particles serving as condensation nuclei. After the condensation of the vapor has been completed, the particles become water droplets that the particles are enclosed in the condensed water. The particles can be easily measured through the simple optical instrument, because these water droplets are very large. However, since the measurement of the particles according to a conventional condensation particle counter in which the particles grow by such an expansion process should be intermittently made, there is a problem in that continuous measurement of the particles is greatly restricted. Accordingly, this technology has been hardly employed at present.

According to the second technology, hot air with saturated water vapor and cold air with the particles are mixed with each other. Thus, supersaturated vapor is formed in a region where the hot and cold air is mixed. Even in such a case, the supersaturated vapor is also condensed around the particles serving as condensation nuclei in the same way as the first technology. Such a type of condensation particle counter is called a mixing type condensation particle counter. However, very high supersaturation may be formed partly in the mixing type condensation particle counter, and thus, the vapor is spontaneously condensed into the water droplets even though the particles used for the condensation nuclei are not provided therein. Therefore, there is also a problem in that the measurement of the number of the particles is inaccurate. Accordingly, this technology has been utilized only in some restricted fields.

The third technology is a conductive cooling type condensation particle counter of which constitution is shown in FIG. 1. The constitution of the conductive cooling type condensation particle counter will be explained with reference to FIG. 1. Alcohol 12 is contained in a storage pool 10, and a cylindrical absorbing member 22 is attached to an inner wall of a saturator 20 which is integrally formed with and extended from the storage pool 10. The alcohol 12 is absorbed into the absorbing member 22 which is made of porous material such as nonwoven fabric and of which one end 22a is immersed into the alcohol within the storage pool 10, and thus, the other end 22b of the absorbing member is caused to be wetted by means of a capillary phenomenon. At an outer wall of the saturator 20 is installed a heater 26 for heating the alcohol permeated into the absorbing member 22 to about 35° C. A condenser 30 is located downstream of the saturator 20 and is provided with a thermo-electric cooler 32 which causes the condenser 30 to be kept at a temperature of about 10° C. for condensing alcohol vapor. In order to sense and measure the grown particles, a well-known optical instrument 50, which comprises an assembly of mirrors or lenses and utilizes a laser or a semiconductor laser as a light source, is located in the vicinity of a leading end of the condenser 30. Further, a flowmeter 60 for regulating a flow rate of the grown particles by means of opening/closing operation of a valve (not shown) and a vacuum pump 70 for sucking the grown particles thereinto are successively installed downstream of the condenser 30 in a state where a pipe 62 is interposed therebetween.

The operation of the conventional conductive cooling type condensation particle counter constructed as such will be explained as follows. First, air with the ultra-fine particles floating therein (hereinafter, referred to as "aerosol") is supplied into the saturator 20, which is kept at the temperature of 35° C. by the heater 26, through an inlet 24 of the saturator 20, and then, it is saturated with the alcohol 12. The alcohol-saturated air continues to flow downstream, and it passes through the condenser 30 corresponding to a cold region of which temperature is maintained at 10° C. The alcohol-saturated air passing through the condenser 30 is supersaturated, and the alcohol is then condensed around the particles in the air so that the particles become grown. The grown particles become larger to their sizes of about 12 µm and are then discharged from the condenser 30. Thus, the optical instrument 50 can readily measure the number of the particles. Furthermore, the grown particles are sucked by the vacuum pump 70, and the flow rate of the particles sucked into the vacuum pump 70 is regulated by the flowmeter 60.

In case of the third type or conductive cooling type condensation particle counter, the thermo-electric cooler used for keeping the condenser at the low temperature of 10° C. is poor in view of a coefficient of performance for removing heat from the condenser by using electricity, and thus, the cooler is good for removing a small quantity of heat from the condenser but inappropriate for removing a large quantity of heat from the condenser. Accordingly, a capacity of the condensation particle counter used commonly and currently is about 0.3 to 1.0 liter/min since it is difficult to cool down a large quantity of air. In particular, in case of the semiconductor clean rooms where it is necessary to sample the particles at a high flow rate, a need for a condensation particle counter capable of sampling the particles at the high flow rate has been required for a long time. However, suitable equipment has not yet been developed. In addition, if the water is used as an operating liquid, the pure ultra-fine particles are merely discharged toward the outside of the condenser since the water vapor passing through the condenser is first condensed at an inner wall surface of the low-temperature condenser without a condensing process in which the vapor is condensed around the particles serving as the nuclei. Thus, there is a problem in that the ultra-fine particles cannot be measured through the optical instrument. That is, the conductive cooling type condensation particle counter has a disadvantage in that only the alcohol must be utilized as the operating liquid. In particular, since the alcohol becomes a pollution source, the conductive cooling type condensation particle counter in which the alcohol should be used as the operating liquid is not suitable for a semiconductor fabrication process.

DISCLOSURE OF INVENTION

An object of the present invention is to provide a condensation particle counter capable of readily and quickly counting ultra-fine particles floating in air.

Another object of the present invention is to provide a condensation particle counter in which various operating liquids can be employed and which can be applied to semiconductor clean rooms where a clean state should be maintained without any contamination.

A further object of the present invention is to provide a condensation particle counter in which the number of particles can be measured at a high flow rate.

In order to achieve the aforementioned objects, the condensation particle counter of the present invention comprises a storage pool with an operating liquid contained therein, a saturator integrally formed with the storage pool and having an absorbing member provided therein to come into contact with the operating liquid for absorbing the operating liquid and a heater installed at an outer wall thereof for forming the operating liquid into vapor, a capillary located downstream of the saturator for condensing the vapor therein to grow particles, an optical instrument installed adjacent to an outlet of the capillary for counting the grown particles, and a suction means located downstream of the capillary for sucking the grown particles therein.

BEST MODE FOR CARRYING OUT THE INVENTION

Hereinafter, a preferred embodiment of a condensation particle counter according to the present invention will be explained in detail with reference to the accompanying drawings.

Figure 1:
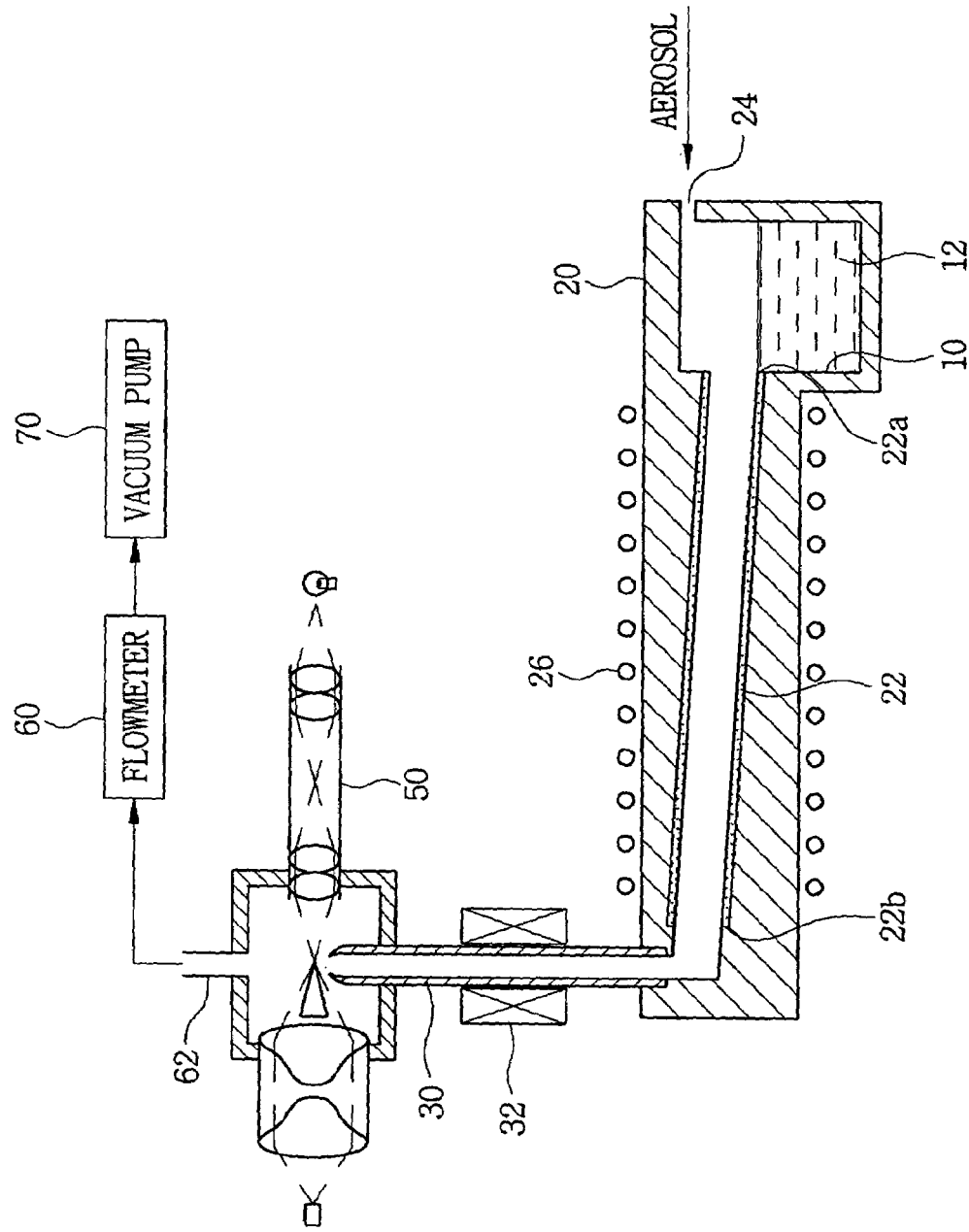
FIG. 1 is a sectional view showing the constitution of a conventional condensation particle counter.
Figure 2:
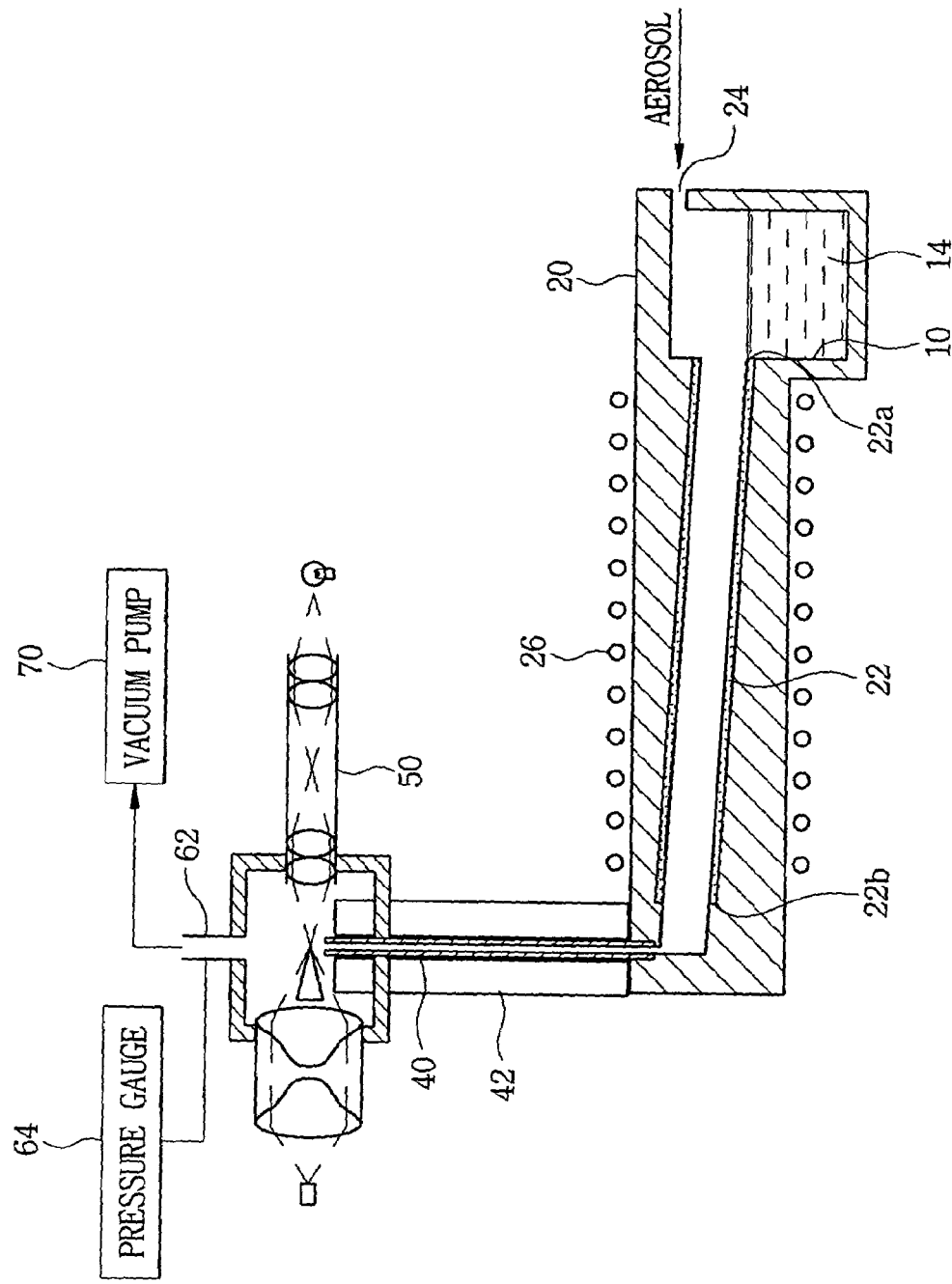
FIG. 2 is a sectional view showing the constitution of a condensation particle counter according to the present invention.

FIG. 2 is a sectional view showing the constitution of the condensation particle counter according to the present invention. In FIG. 2, like elements, which are the same as those of the conventional condensation particle counter shown in FIG. 1, are denoted by like reference numerals.

An operating liquid 14 is contained in a storage pool 10, and a cylindrical absorbing member 22 is attached to an inner wall of a saturator 20 integrally formed with the storage pool 10. In the present invention, various liquids including alcohol and water can be utilized as the operating liquid. The operating liquid is absorbed into the absorbing member 22 which is made of porous material such as nonwoven fabric and of which one end 22a is immersed into the operating liquid within the storage pool 10, and thus, the other end 22b of the absorbing member is caused to be wetted. At an outer wall of the saturator 20 is installed a heater 26 for heating the operating liquid permeated into the absorbing member 22. The heater 26 heats up the operating liquid either to about 35° C. in a case where the operating liquid is alcohol or to about 70° C. in a case where the operating liquid is water.

A capillary 40 is located downstream of the saturator 20, and an insulating member 42 is installed at an outer wall of the capillary 40 in order to shut out heat flow between the capillary and the environment. In the capillary 40, vapor of the operating liquid is condensed and the particles grow. If supersonic flow is accomplished in the capillary 40, a mass flow rate of the vapor including the particles becomes constant. In such a case, the flowmeter 60 provided in the conventional condensation particle counter shown in FIG. 1 is not required. In order to sense and count the grown particles, a well-known optical instrument 50 is located in the vicinity of a leading end of the capillary 40.

A vacuum pump 70 for sucking the grown particles therein is installed downstream of the capillary 40 in a state where a pipe 62 is interposed therebetween. A well-known pressure gauge 64 for detecting sufficient pressure drop is installed at the pipe 62. If the pressure within the capillary 40 is reduced sufficiently to 0.5 atm or less by means of the vacuum pump 70, the supersonic flow becomes accomplished in the capillary 40. If the pressure within the capillary 40 is maintained at 0.5 atm or less by means of the vacuum pump 70, vapor temperature within the capillary 40 is greatly lowered through adiabatic expansion of vapor so that the vapor is maintained at a supersaturated state. Thus, the vapor is condensed around the particles serving as the nuclei, and then, the particles become grown.

Hereinafter, the operation of the condensation particle counter according to the present invention will be explained. First, aerosol is supplied into the saturator 20, which is maintained at a predetermined temperature by the heater 26, through an inlet 24 of the saturator. Then, the air is saturated with the operating liquid such as the alcohol or water. The air saturated with the operating liquid continues to flow downstream, and it passes through the capillary 40. The air, which has been saturated with the operating liquid and passes through the capillary 40, is supersaturated by an operation of the vacuum pump 70, and the vapor is then condensed around the particles so that the particles become grown. As described above, a growing process of the particles is accomplished in such a manner that when the vacuum pump 70 causes the capillary to be kept at a very low pressure, the temperature of the vapor is greatly lowered through the adiabatic expansion of the vapor within the capillary so that the vapor is caused to be kept at the supersaturated state. At this time, if the supersonic flow of the vapor is also accomplished in the capillary 40, the mass flow rate of the vapor including the particles becomes constant. The particles grown by vapor condensation become larger and are then discharged from the capillary 40. Thus, the optical instrument 50 can readily count the number of the particles. Then, the grown particles are sucked by the vacuum pump 70.

Although the invention has been described with respect to the preferred embodiment, the scope of protection sought in the present invention is not limited thereto. It will be understood by the skilled in the art that specific design and constitution described in the preferred embodiment is one example of the present invention and that various changes and modifications may be made thereto without departing from the spirit and scope of the invention as defined in the appended claims.

INDUSTRIAL APPLICABILITY

As described above, the condensation particle counter of the present invention can quickly and readily count the ultra-fine particles floating in the air, and various operating liquids such as water as well as alcohol can also be utilized in the condensation particle counter. Furthermore, the condensation particle counter can be applied even to the semiconductor clean rooms. Finally, the number of particles can be measured at a high flow rate.

What is claimed is:

1. A condensation particle counter, comprising:
    a storage pool with an operating liquid contained therein;
    a saturator integrally formed with the storage pool and having an absorbing member provided therein to come into contact with the operating liquid for absorbing the operating liquid and a heater installed at an outer wall thereof for forming the operating liquid into vapor;
    a capillary located downstream of the saturator for condensing the vapor therein to grow particles;
    an optical instrument installed adjacent to an outlet of the capillary for counting the grown particles; and
    a suction means located downstream of the capillary for sucking the grown particles thereinto;
    said counter further comprising the operating liquid, wherein a temperature of the vapor of said operating liquid in said capillary is reduced substantially through adiabatic expansion of the vapor, rather than through heat exchange with the environment.

2. The condensation particle counter as claimed in claim 1, further comprising an insulating member for insulating the capillary from the environment.

3. The condensation particle counter as claimed in claim 1, wherein the suction means is a vacuum pump.

4. The counter of claim 1, wherein said capillary has a substantially constant inner diameter throughout an entire longitudinal extent thereof.

5. The counter of claim 1, wherein said suction means are configured to lower a pressure of the vapor within said capillary to a pressure level sufficient to cause a supersonic flow in said capillary.

6. The counter of claim 5, wherein said pressure level is 0.5 atm or less.

7. The counter of claim 2, wherein said capillary further has an inlet opposite to said outlet and a middle section positioned between said inlet and outlet and continuous to both said inlet and outlet;
    said inlet and outlet extending through outer walls of said saturator and said optical instrument, respectively, and said middle section extending between said outer walls;
    an entirety of said middle section being substantially free of heat exchange with the environment due to said insulating member.

8. The counter of claim 7, wherein said insulating member is received in said optical instrument to surround at least partially the outlet of said capillary.

9. The counter of claim 1, further comprising water as the operating liquid.

10. A condensation particle counter, consisting essentially of:
    a storage pool with an operating liquid contained therein;
    a saturator in fluid communication with the storage pool, said saturator having an absorbing member in contact with the operating liquid for absorbing the operating liquid and a heater for converting the operating liquid into vapor;
    a capillary tube located downstream of the saturator for condensing the vapor on particles to form and grow droplets around the particles;
    an optical instrument installed adjacent to an outlet of the capillary for counting the grown droplets;
    a suction source located downstream of the capillary tube for sucking the grown droplets out of the capillary tube; and
    an insulator for insulating the capillary tube from a surrounding environment;
    wherein said suction source is configured to lower a pressure of the vapor within said capillary tube to a pressure level sufficient to cause a supersonic flow in said capillary tube and to reduce a temperature of the vapor of said operating liquid in said capillary substantially through adiabatic expansion of the vapor, rather than through heat exchange with the environment.

11. The counter of claim 10, wherein the outlet of said capillary tube is cylindrical and has substantially parallel walls when seen in cross section.

12. The counter of claim 10, comprising water as the operating liquid.

13. The counter of claim 10, wherein said capillary tube further has an inlet opposite to said outlet and a middle section positioned between said inlet and outlet and continuous to both said inlet and outlet;
    said inlet and outlet extending through outer walls of said saturator and said optical instrument, respectively, and said middle section extending between said outer walls;
    an entirety of said middle section being substantially free of heat exchange with the environment due to said insulator.

14. A condensation particle counter, comprising:
    a storage pool with an operating liquid contained therein;
    a saturator in fluid communication with the storage pool for converting the operating liquid into vapor;
    a capillary tube located downstream of the saturator for condensing the vapor on particles to form and grow droplets around the particles, wherein said capillary tube has opposite first and second ends and a middle section positioned between said ends and continuous to both said ends;
    an optical instrument installed adjacent to the first end of the capillary for counting the grown droplets;
    a suction source located downstream of the capillary tube for sucking the grown droplets out of the capillary tube; and
    an insulator for insulating the capillary tube from a surrounding environment;
    wherein said first and second ends of the capillary tube extend through outer walls of said saturator and said optical instrument, respectively, and said middle section extending between said outer walls, an entirety of said middle section being substantially free of heat exchange with the environment due to said insulator.

15. The counter of claim 14, wherein said saturator has an absorbing member in contact with the operating liquid for absorbing the operating liquid and a heater for converting the absorbed operating liquid into said vapor.

16. The counter of claim 14, wherein said capillary has a substantially constant inner diameter throughout an entire longitudinal extent thereof.

17. The counter of claim 14, wherein said suction source is configured to lower a pressure of the vapor within said capillary tube to a pressure level sufficient to cause a supersonic flow in said capillary tube.

18. The counter of claim 14, further comprising the operating liquid, wherein a temperature of the vapor of said operating liquid in said capillary tube is reduced substantially through adiabatic expansion of the vapor, rather than through heat exchange with the environment.

* * * * *